(12) United States Patent
Ding et al.

(10) Patent No.: US 11,052,231 B2
(45) Date of Patent: Jul. 6, 2021

(54) MICROARRAY FOR DELIVERY OF THERAPEUTIC AGENT AND METHODS OF USE

(71) Applicant: CORIUM INTERNATIONAL, INC., Menlo Park, CA (US)

(72) Inventors: Zhongli Ding, Sunnyvale, CA (US); Guohua Chen, Sunnyvale, CA (US); Ashutosh Shastry, Santa Clara, CA (US); Robert Wade Worsham, Cupertino, CA (US); Parminder Singh, Union City, CA (US)

(73) Assignee: Corium, Inc., Grand Rapids, MI (US)

( * ) Notice: Subject to any disclaimer, the term of this patent is extended or adjusted under 35 U.S.C. 154(b) by 370 days.

(21) Appl. No.: 14/137,899

(22) Filed: Dec. 20, 2013

(65) Prior Publication Data

US 2014/0180201 A1     Jun. 26, 2014

Related U.S. Application Data

(60) Provisional application No. 61/745,513, filed on Dec. 21, 2012.

(51) Int. Cl.
| | | |
|---|---|---|
| *A61M 37/00* | (2006.01) | |
| *A61K 9/00* | (2006.01) | |
| *B29C 70/78* | (2006.01) | |
| *B81C 1/00* | (2006.01) | |
| *B29C 43/02* | (2006.01) | |

(52) U.S. Cl.
CPC ....... *A61M 37/0015* (2013.01); *A61K 9/0021* (2013.01); *B29C 43/021* (2013.01); *B29C 70/78* (2013.01); *B81C 1/00357* (2013.01); *A61M 2037/0046* (2013.01); *A61M 2037/0053* (2013.01); *B29C 2043/025* (2013.01)

(58) Field of Classification Search
CPC .............. A61M 37/00; A61M 37/0015; A61M 2037/0023; A61M 2037/0046; A61M 2037/0053; A61M 2037/0061; A61K 9/0021
USPC .......................................... 604/46, 173, 272
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Makaida et al. "Poly Lactic-co-Glycolic Acid (PLGA) as Biodegradable Controlled Drug Delivery Carrier". Sep. 1, 2011, Polymers (Basel), 3(3): 1377-1397.*

(Continued)

*Primary Examiner* — Jason E Flick
(74) *Attorney, Agent, or Firm* — McDermott Will & Emery LLP; Judy M. Mohr; Edward J. DesJardins

(57) ABSTRACT

Devices and methods for using and manufacturing microstructure arrays having at least a detachable distal area are described.

35 Claims, 9 Drawing Sheets

(56) References Cited

U.S. PATENT DOCUMENTS

| | | |
|---|---|---|
| 3,704,194 A | 11/1972 | Harrier |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Matsushita et al. |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Ericksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |

(56) References Cited

U.S. PATENT DOCUMENTS

| | | |
|---|---|---|
| 6,375,627 B1 | 4/2002 | Mauze et al. |
| 6,375,870 B1 | 4/2002 | Visovsky et al. |
| 6,375,978 B1 | 4/2002 | Kliener et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 | 5/2006 | Frazier et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Gharty-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 | 1/2017 | Woolfsen et al. |
| 9,687,640 B2 | 6/2017 | Trautman et al. |
| 9,687,641 B2 | 6/2017 | Singh et al. |
| 9,962,534 B2 | 5/2018 | Chen et al. |
| 10,195,409 B2 | 2/2019 | Bourne et al. |
| 10,238,848 B2 | 3/2019 | Singh et al. |
| 10,245,422 B2 | 4/2019 | Le et al. |
| 10,384,045 B2 | 8/2019 | Ding et al. |
| 10,384,046 B2 | 8/2019 | Bayramov et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 | 3/2004 | Mazess et al. |
| 2004/0062813 A1 | 4/2004 | Cormier et al. |
| 2004/0087893 A1 | 5/2004 | Kwon |

(56) References Cited

U.S. PATENT DOCUMENTS

| | | |
|---|---|---|
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0224377 A1 | 9/2007 | Leimbacher et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0063866 A1 | 3/2008 | Allen et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Fredrickson et al. |
| 2008/0200883 A1 | 8/2008 | Tomono |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0262444 A1 | 10/2008 | Takada |
| 2008/0269685 A1* | 10/2008 | Singh ............... A61K 9/0021 |
| | | 604/173 |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2009/0234301 A1 | 9/2009 | Tomono |
| 2010/0004608 A1 | 1/2010 | Hamamoto et al. |
| 2010/0028390 A1 | 2/2010 | Cleary et al. |
| 2010/0200494 A1* | 8/2010 | Storer ............... B01D 39/1623 |
| | | 210/510.1 |
| 2010/0228203 A1 | 9/2010 | Quan et al. |
| 2010/0247698 A1 | 9/2010 | Zhang et al. |
| 2011/0006458 A1* | 1/2011 | Sagi ............... A61M 37/0015 |
| | | 264/319 |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0165236 A1 | 7/2011 | Chow et al. |
| 2011/0177139 A1 | 7/2011 | Hyungil et al. |
| 2011/0195124 A1 | 8/2011 | Jin |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1 | 12/2011 | Kaufmann et al. |
| 2011/0306853 A1 | 12/2011 | Black et al. |
| 2012/0052120 A1 | 3/2012 | Castor |
| 2012/0123297 A1 | 5/2012 | Brancazio |
| 2012/0123387 A1 | 5/2012 | Gonzalez et al. |
| 2012/0126297 A1 | 5/2012 | Brancazio |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0150822 A1 | 6/2013 | Ross |
| 2013/0156849 A1* | 6/2013 | de Fougerolles ...... A61K 48/00 |
| | | 424/450 |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2014/0330198 A1 | 11/2014 | Zhang et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0015952 A1 | 1/2016 | Omachi et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0050010 A1 | 2/2017 | Mcallister et al. |
| 2017/0217656 A1 | 8/2017 | Yamada |
| 2017/0281535 A1 | 10/2017 | Singh et al. |
| 2017/0361079 A1 | 12/2017 | Trautman et al. |
| 2019/0001109 A1 | 1/2019 | Kim et al. |
| 2019/0184147 A1 | 6/2019 | Singh et al. |
| 2019/0184148 A1 | 6/2019 | Le et al. |
| 2019/0336741 A1 | 11/2019 | Bayramov et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 1377338 A2 | 1/2004 |

(56) References Cited

FOREIGN PATENT DOCUMENTS

| | | |
|---|---|---|
| EP | 1 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2007-190112 A | 1/2006 |
| JP | 2006/271781 A | 10/2006 |
| JP | 2006-341089 A | 12/2006 |
| JP | 2007-130030 A | 5/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1996/038174 A1 | 12/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030281 A1 | 4/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/020034 A2 | 3/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/044333 A2 | 5/2005 |
| WO | WO 2005/046769 A2 | 5/2005 |
| WO | WO 2005/065765 A1 | 7/2005 |
| WO | WO 2005/067889 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |

(56) References Cited

FOREIGN PATENT DOCUMENTS

| | | |
|---|---|---|
| WO | WO 2008/093679 A1 | 8/2008 |
| WO | WO 2008/130587 | 10/2008 |
| WO | WO 2008/139648 A1 | 11/2008 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/101639 A2 | 8/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2016/149152 A2 | 9/2016 |
| WO | WO 2017/004067 A1 | 1/2017 |
| WO | WO 2017/116076 A1 | 7/2017 |

OTHER PUBLICATIONS

Avcin et al., "Subcutaneous nodule after vaccination with an aluminum-containing vaccina", Acta Dermatoven, APA, vol. 17, No. 4, pp. 182-184 (2008).
Corbett et al., "Skin vaccination against cervical cancer associated human papillomavirus with a novel micro-projection array in a mouse model", PLOS one, vol. 5, No. 10, pp. 1-9 (2010).
Database WPI / Thomson, Accession No. 2014-V89218, Gao et al., "Soluble microneedle patch useful for transdermal administration of vaccine, comprises water-soluble polymer material as matrix material and soluble microneedle main portion", Application No. CN104027324A, Tech Inst Phys. & Chem. Chinese Acad., 3 pages (2014).
"Extend", Merriam-Webster Online Dictionary, 6 pages, Downloaded on Sep. 7, 2010 from <http://www.merriam-webster.com/dictionary/extend>.
"Extend", Macmillan Online Dictionary, 5 pages, Downloaded on Sep. 7, 2010 from <http://www.macmillandictionary.com/dictionary/american/extend>.
Ghosh et al., "Influence of critical parameters of nanosuspension formulation on permeability of a poorly soluble drug through the skin-A case study", vol. 14, No. 3, pp. 1108-1117 (2013).
Guo et al., "Enhanced transcutaneous immunization via dissolving microneedle array loaded with liposome encapsulated antigen and adjuvant", Int. J. Pharm., vol. 447, No. 1-2, pp. 22-30 (2013).
Gupta, "Aluminum compounds as vaccine adjuvants", Adv. Drug Deliv. Rev., vol. 32, No. 3, pp. 155-172 (1998) Abstract Only.
Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).
International Search Report from International Patent Application No. PCT/US2015/047563 dated Nov. 20, 2015.
International Search Report from International Patent Application No. PCT/US2015/048161 dated Nov. 26, 2015.
International Search Report from International Patent Application No. PCT/US2015/059559 dated Jan. 21, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Kuroda et al., "Particulate adjuvant and innate immunity: past achievements, present findings, and future prospects", Int. Rev. Immunol., vol. 32, No. 2, pp. 209-220 (2013).
Munks et al., "Aluminum adjuvants elicit fibrin-dependent extracellular traps in vivo", Blood, vol. 116, No. 24, pp. 5191-5199 (2010).
Petrovsky and Aguilar, "Vaccine adjuvants: current state and future trends", Immunol. Cell Biol., vol. 82, No. 5, pp. 488-496 (2004).
Pittman, "Aluminum-containing vaccine associated adverse events: role of route of administration and gender", Vaccine, vol. 20, pp. s48-s50 (2002).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
Vitiello et al., "Development of a lipopeptide-based therapeutic vaccine to treat chronic HBV infection", J. Clin. Invest., vol. 95, pp. 341-349 (1995).
White et al., "Studies on antibody production. III. The alum granuloma", J. Exp. Med., vol. 102, No. 1, pp. 73-82 (1955).
International Search Report from International Patent Application No. PCT/US2011/035221 dated Jan. 10, 2012, application now published as International Publication No. WO2011/140240 on Nov. 10, 2011.
International Search Report from International Patent Application No. PCT/US2016/039864 dated Sep. 23, 2016.
Lutrol F 68 NF, BASF Pharma Ingredients, accessed from the internet on Sep. 5, 2016 from http://www2.basf.us/Pharma/pdf/Lutrol_F_68.pdf.
Prausnitz, "Microneedle-based vaccines", Curr. Top. Microbiol. Immunol., vol. 333, pp. 369-393 (2009).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.
Polysorbate 80, Material Safety Data Sheet, CAS#: 9005-65-6, Science Lab.com, Inc., 14025 Smith Rd., Houston, Texas 77396, 5 pages, Last updated May 21, 2013.
Huh et al., "PLGA-PEG Block Copolymers for Drug Formulations", Drug Dev. Deliv., vol. 3, pp. 1-11 (2003).
International Search Report from International Patent Application No. PCT/US2019/039028 dated Sep. 13, 2019.
Locatelli et al., "Biodegradable PLGA-b-PEG polymeric nanoparticles: synthesis, properties, and nanomedical applications as drug delivery system", J. Nanopart. Res., vol. 14, No. 1316, pp. 1-17 (2012).
"Eudragit EPO Readymix—Taste masking and moisture protection have never been easier" Evonik Industries, Evonik Industries AG, Pharma Polymers & Services, Nov. 2014.
International Search Report from International Patent Application No. PCT/US2014/022836 dated May 9, 2015.
International Search Report from International Patent Application No. PCT/US2014/021841 dated Aug. 11, 2014.
International Search Report from International Patent Application No. PCT/US2014/022087 dated May 23, 2014.
International Search Report from International Patent Application No. PCT/US2014/022859 dated May 26, 2014.
International Search Report from International Patent Application No. PCT/US2014/026179 dated Jul. 18, 2014.
International Search Report from International Patent Application No. PCT/US2014/029601 dated Jul. 1, 2014.
Chun, et al., "An array of hollow microcapillaries for the controlled injection of genetic materials into animal/plant cells," IEEE Workshop on Micro Electro Mechanical Systems, pp. 406-411, (1999).
"Extend", Merriam-Webster Online Dictionary, <http://www.merriam-webster.com/dictionary/extend>.
"Extend", Macmillan Online Dictionary, <http://www.macmillandictionary.com/dictionary/american/extend>.

(56) References Cited

OTHER PUBLICATIONS

Henry, et al., "Micromachined microneedles for transdermal delivery of drugs", IEEE Workshop on Micro Electro Mechanical Systems, New York, NY, pp. 494-498, (1998).

Henry, et al., "Microfabricated microneedles: A novel approach to transdermal drug delivery", J. Pharmaceutical Science, vol. 87, No. 8, pp. 922-925, (1998).

"Heparin Pregnancy and Breast Feeding Warnings", Drugs.com, Accessed Oct. 8, 2009, <http://www.drugs.com/pregnancy/heparin.html>.

International Search Report from International Patent Application No. PCT/US2000/015612 dated Sep. 7, 2000.

International Search Report from International Patent Application No. PCT/US2000/015613 dated Sep. 6, 2000.

International Search Report from International Patent Application No. PCT/US2000/015614 dated Sep. 6, 2000.

International Search Report from International Patent Application No. PCT/US2001/031977 dated Apr. 29, 2002.

International Search Report from International Patent Application No. PCT/US2001/031978 dated Apr. 29, 2002.

International Search Report from International Patent Application No. PCT/US2002/014624 dated Sep. 3, 2002.

International Search Report from International Patent Application No. PCT/US2002/029228 dated Apr. 23, 2003.

International Search Report from International Patent Application No. PCT/US2002/029245 dated Dec. 27, 2002.

International Search Report from International Patent Application No. PCT/US2004/005382 dated Nov. 25, 2004.

International Search Report from International Patent Application No. PCT/US2004/017255 dated May 24, 2005.

International Search Report from International Patent Application No. PCT/US2005/009854 dated Jul. 3, 2008.

International Search Report from International Patent Application No. PCT/US2008/000824 dated Jul. 18, 2008.

International Search Report from International Patent Application No. PCT/US2008/004943 dated Jun. 9, 2009, application now published as International Publication No. WO2008/130587 Oct. 30, 2008.

International Search Report from International Patent Application No. PCT/US2008/011635 dated Dec. 19, 2008, application now published as International Publication No. WO2009/048607 on Apr. 16, 2009.

International Search Report from International Patent Application No. PCT/US2010/032299 dated Dec. 10, 2010, application now published as International Publication No. WO2010/124255 on Oct. 28, 2010.

International Search Report from International Patent Application No. PCT/US2013/077281 dated Mar. 4, 2013.

Matriano, et al., "Macroflux(R) microprojection array patch technology: A new and efficient approach for intracutaneous immunization", Pharm. Res., vol. 19, No. 1, pp. 63-70, (2002).

McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.

Mikszta, et al., "Improvred genetic immunization via micromechanical disruption of skin-barrier function and targeted epidermal delivery", Nat. Med., vol. 8, No. 4, pp. 415-419, (2002).

Mikszta, et al., "Protective immunization against inhalation anthrax: A comparison of minimally invasive delivery platforms", J. Inf. Dis., vol. 191, No. 2, pp. 278-288, (2005).

Papautsky, et al., "Micromachined Pipette Arrays," MPA, Proceedings—19th international Conference—IEEE/EMBS, Chicago IL, USA, pp. 2281-2284 (1997).

Park et al., "Biodegradable polymer microneedles: Fabrication, mechanics, and transdermal drug delivery", J. Contr. Rel., vol. 104, pp. 51-66 (2005).

Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).

Prausnitz, et al., "Transdermal transport efficiency during skin electroporation and iontophoresis", J. Contr. Release, vol. 38, pp. 205-217, (1996).

Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).

Rydberg, et al., "Low-molecular-weight heparin preventing and treating DVT", Am. Fam. Physician, vol. 59, No. 6, pp. 1607-1612, (1999).

Sivamani, et al., "Microneedles and transdermal applications", Exp. Opin. Drug Del., vol. 4, No. 1, pp. 19-25, (2007).

Wouters, et al., "Microelectrochemical systems for drug delivery", Electrochimica Acta., vol. 42, pp. 3385-3390, (1997).

Xia, et al., "Soft Lithography", Angew. Chem. Int, Ed., vol. 37, pp. 551-575, (1998).

Xia, et al., "Soft Lithography", Annu. Rev. Mater. Sci., vol. 28, pp. 153-184 (1998).

Yang et al., "A scalable fabrication process of polymer microneedles", Int. J. Nanomedicine, vol. 7, pp. 1415-1422 (2012).

\* cited by examiner

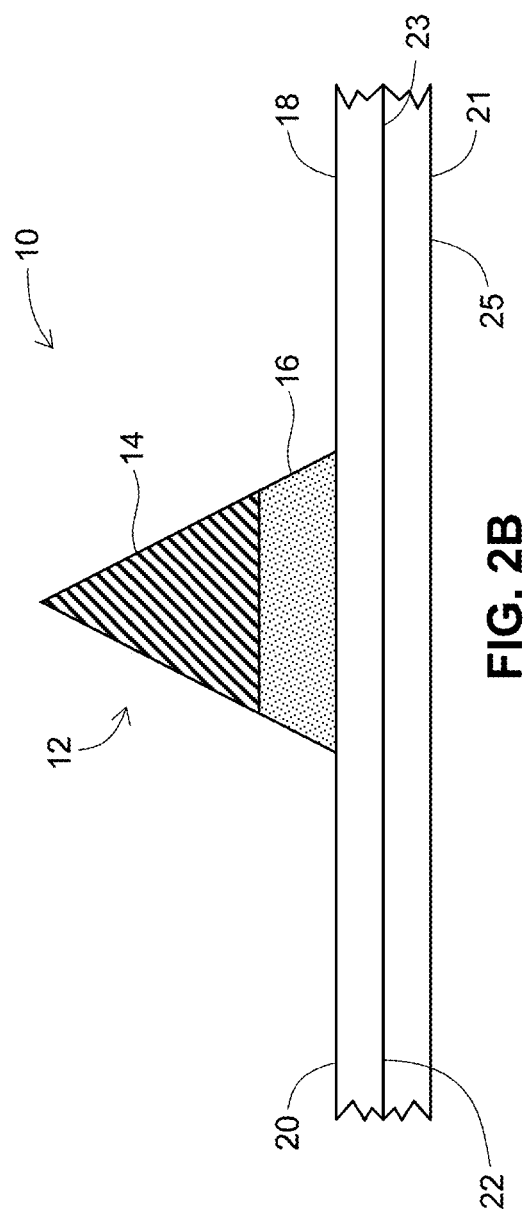

MICROARRAY FOR DELIVERY OF THERAPEUTIC AGENT AND METHODS OF USE

CROSS-REFERENCE TO RELATED APPLICATIONS

This application claims the benefit of U.S. Provisional Application No. 61/745,513, filed Dec. 21, 2012, which is incorporated herein by reference in its entirety.

TECHNICAL FIELD

The disclosure relates generally to a method and delivery system for transdermally administering a therapeutic agent or drug or vaccine using an array of microstructures, and related features thereof.

BACKGROUND

Arrays of microneedles were proposed as a way of administering drugs through the skin in the 1970s, for example in expired U.S. Pat. No. 3,964,482, Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A detailed description of the fabrication of a microneedle array made of polyglycolic acid is found in Jung-Hwan Park et al., "Biodegradable polymer microneedles: Fabrication, mechanics, and transdermal drug delivery," J. of Controlled Release, 104:51-66 (2005).

A layered microstructure array has been described for hPTH delivery (U.S. Patent No. 2011/0276028) comprising a fast dissolving drug-in-tip distal layer and a backing layer formed of an insoluble biodegradable polymer.

Many drugs require sustained delivery for a prolonged period of time including hours, days, weeks, etc. Wearing a drug delivery device for the extended duration required for sustained or complete drug delivery from an array may be inconvenient and/or painful. A need exists for a device that is effective to provide delivery of a therapeutic agent that is sustained and/or for a prolonged period of time with minimal inconvenience and/or pain.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect of the invention, an array of microstructures is provided comprising an approximately planar base and a plurality of microstructures. In an embodiment, at least a portion of the microstructures are comprised of one or more layers arranged roughly parallel to the plane of the base. In one embodiment, at least a portion of the microstructures is configured to detach, separate, or break from the base.

In a further aspect of the invention, an array of microprotrusions is formed by (a) dispensing a selected formulation atop a mold with a plurality of cavities corresponding to the negative of the microprotrusions, (b) transferring the formulation into the plurality of cavities, (c) drying the formulation into the cavities, and (d) de-molding the resulting array from the mold.

In one aspect microstructure apparatuses are contemplated. In an embodiment, the microstructure apparatus comprises a backing having a first surface and a second surface opposed thereto; a microstructure array comprising a plurality of microstructures extending outwardly from the first surface of the backing; the microstructures comprising a biodegradable distal layer and at least one proximal layer positioned between the distal layer and the first surface of the backing; the distal layer comprised of at least one therapeutic agent and at least one polymer; and wherein at least a portion of the distal layer detaches readily upon insertion of the array into skin.

In embodiments, the distal layer comprises at least one hydrophobic polymer. In further embodiments, the distal layer comprises at least one polymer comprises at least one hydrophobic polymer and about 0-99% of at least one hydrophilic polymer. In even further embodiments, the distal layer comprises at least one polymer that comprises at least one hydrophobic polymer and about 0-50% of a hydrophilic polymer. In additional embodiments, the distal layer comprises at least one polymer that comprises at least one hydrophobic polymer and about 0-20% of a hydrophilic polymer.

In further embodiments, at least one therapeutic agent is a small molecule drug at least partially soluble with the at least one polymer in a solvent or co-solvent. In embodiments, the distal layer comprises about 1-99% of the small molecule drug. In further embodiments, the distal layer comprises about 1-50% of the small molecule drug. In more embodiments, the distal layer comprises about 5-40% of the small molecule drug. In additional embodiments, the distal layer comprises about 10-30% of the small molecule drug.

In more embodiments, at least one therapeutic agent is dispersed in the distal layer. In embodiments, the distal layer comprises about 1-90% of the dispersed agent. In further embodiments, the distal layer comprises about 1-50% of the dispersed agent. In yet further embodiments, the distal layer comprises about 10-40% of the dispersed agent. In additional embodiments, the distal layer comprises about 20-30% of the dispersed agent.

In embodiments, the at least one polymer is in a glass state at room temperature. In further embodiments, the at least one polymer has a glass transition temperature (Tg) at or above about body temperature.

In embodiments, at least about 10% of the distal layer detaches readily upon insertion of the array into skin. In further embodiments, at least about 50% of the distal layer detaches readily upon insertion of the array into skin. In additional embodiments, at least about 70% of the distal layer detaches readily upon insertion of the array into skin. In yet more embodiments, at least about 90% of the distal layer detaches readily upon insertion of the array into skin. In other embodiments, about 100% of the distal layer detaches readily upon insertion of the array into skin.

In embodiments, at least a portion of the microstructures have a first cross-dimensional diameter that is larger than a second cross-dimensional diameter. In other embodiments, at least a portion of the microstructures have a cross-dimensional shape selected from the group consisting of a diamond, a rectangle, and an oval. In further embodiments, at least a portion of the microstructures have an asymmetrical cross-dimensional shape.

In embodiments, a concentration of the at least one polymer in a polymer casting solution used to form the microstructures is lower than an entanglement concentration ($C_E$) for the polymer. In additional embodiments, a concentration of the at least one polymer in a polymer casting solution used to form the microstructures is at a $C_E$ for the polymer.

In embodiments, at least a portion of the proximal and/or distal layers has a funnel shape.

In further embodiments, at least a portion of the microstructures are affixed to the first surface of the backing.

In additional embodiments, at least a portion of the backing forms the proximal layer. In embodiments, the microstructure apparatus comprises a substrate having a first surface and a second surface opposed thereto, where the second surface of the backing is affixed to the first surface of the substrate.

In additional embodiments, the microstructure apparatus comprises a substrate having a first surface and a second surface opposed thereto; a microstructure array comprising a plurality of microstructures affixed to the first surface of the substrate and extending outwardly therefrom; where the microstructures are comprised of a biodegradable distal layer and a proximal layer positioned between the distal layer and the first surface of the substrate; the distal layer comprised of at least one hydrophobic polymer and at least one therapeutic agent, and wherein at least a portion of the distal layer detaches readily upon insertion of the array into skin.

In further embodiments, the microstructure apparatus comprises a backing having a first surface and a second surface opposed thereto; a microstructure array comprising a plurality of microstructures affixed upon the first surface of the backing and extending outwardly therefrom; the microstructures comprising of a biodegradable distal layer and a proximal layer positioned between the distal layer and the first surface of the backing; the distal layer comprised of at least one polymer and about 1-90% of a therapeutic agent; and wherein at least a portion of the distal layer detaches readily upon insertion of the array into skin.

In other embodiments, the microstructure apparatus comprises a backing having a first surface and a second surface opposed thereto; a microstructure array comprising a plurality of microstructures affixed upon the first surface of the backing and extending outwardly therefrom; the microstructures comprising a biodegradable distal layer and a proximal layer positioned between the distal layer and the first surface of the backing; the distal layer is comprised of at least one polymer and a therapeutic agent, the at least one polymer having a glass transition temperature (Tg) at least above about body temperature; and wherein at least a portion of the distal layer detaches readily upon insertion of the array into skin.

In additional embodiments, the microstructure apparatus comprises a backing having a first surface and a second surface opposed thereto; a microstructure array comprising a plurality of microstructures affixed upon the first surface of the backing and extending outwardly therefrom; the microstructures comprising a biodegradable distal layer and a proximal layer positioned between the distal layer and the first surface of the backing; the distal layer being comprised of at least one polymer having a molecular weight between about 1-100K Da and a therapeutic agent; and wherein at least a portion of the distal layer detaches readily upon insertion of the array into skin.

In more embodiments, the microstructure apparatus comprises a backing having a first surface and a second surface opposed thereto; a microstructure array comprising a plurality of microstructures affixed upon the first surface of the backing and extending outwardly therefrom; the microstructures comprising a biodegradable distal layer and a proximal layer positioned between the distal layer and the first surface of the backing; the distal layer being comprised of at least one polymer and a therapeutic agent; and wherein at least about 10-100% of the distal layer detaches readily upon insertion of the array into skin.

In yet another embodiment, the microstructure apparatus comprises a substrate having a first surface and a second surface opposed thereto; a microstructure array comprising a plurality of microstructures affixed upon the first surface of the substrate and extending outwardly therefrom; the microstructures comprising a biodegradable distal layer and a proximal layer positioned between the distal layer and the first surface of the substrate; the distal layer comprised of at least one polymer and a therapeutic agent, the distal layer having a first cross-dimensional diameter that is larger than a second cross-dimensional diameter; and wherein at least a portion of the distal layer detaches readily upon insertion of the array into skin.

In another aspect, methods of making a microstructure apparatus are contemplated. In one embodiment, the method comprises dissolving or suspending a therapeutic agent in a solvent to form a therapeutic agent solution or suspension; dissolving at least one polymer in a solvent to form a polymer solution; mixing the therapeutic agent solution or suspension and the polymer solution or suspension to form a polymer matrix solution or suspension; dispensing the polymer matrix solution or suspension on a mold having an array of microstructure cavities; followed by pressurization; removing excess solution or suspension polymer matrix on the mold surface; and drying the matrix; and dispensing a basement or backing layer on the mold surface; and drying the basement or backing layer. In an embodiment, the method further comprises affixing the basement or backing layer to a substrate. In further embodiments, the method comprises using a nonwoven or porous film double coated with adhesive to affix the basement or backing layer to a substrate.

Additional embodiments of the present microstructures, arrays, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIGS. 2A-2B are illustrations of exemplary microstructure arrays showing a microstructure having at least a distal layer and a proximal layer on a substrate.

FIG. 5A is a front perspective view and FIG. 5B is a side view of the microstructure.

FIG. 8A depicts a microstructure having a pyramidal tip with a funnel shaped distal portion. FIG. 8B depicts a microstructure having a conical tip, a cylindrical shank and a conical funnel distal portion.

Figure 1:
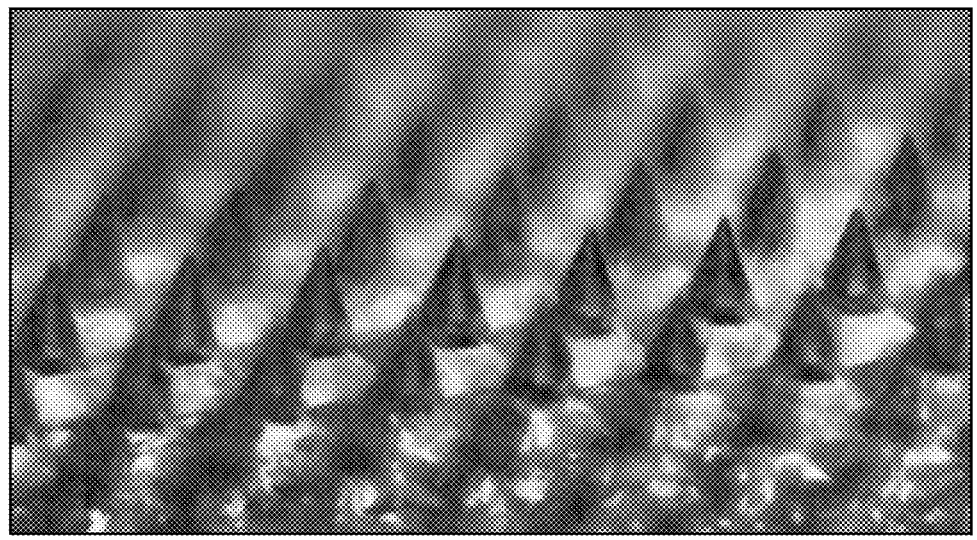
FIG. 1 is a microscopic image of one exemplary microstructure array.

It will be appreciated that the thicknesses and shapes for the various microstructures have been exaggerated in the drawings to facilitate understanding of the device. The drawings are not necessarily "to scale."

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

In describing and claiming the present invention, the following terminology will be used in accordance with the definitions described below.

"Biodegradable" refers to natural or synthetic materials that degrade enzymatically, non-enzymatically or both to produce biocompatible and/or toxicologically safe by-products which may be eliminated by normal metabolic pathways.

As used herein, "body temperature" refers to normal body temperature, which is about 98.6° F.±1-2° F. for the core body temperature of a human. It will be appreciated that normal body temperature will vary slightly depending on the method used to measure and/or the time of day the measurement is made.

"Hydrophobic polymer" as used herein refers to polymers that are insoluble or poorly soluble in aqueous solvents. "Hydrophilic polymer" as used herein refers to polymers that are soluble or substantially soluble in aqueous solvents.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

"Optional" or "optionally" means that the subsequently described circumstance may or may not occur, so that the description includes instances where the circumstance occurs and instances where it does not.

"Substantially" or "essentially" means nearly totally or completely, for instance, 90-95% or greater of some given quantity.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

II. Microstructure Arrays

General features of microstructure arrays suitable for use in the instant arrays and methods are described in detail in U.S. Patent Publication No. 2008/0269685, U.S. Patent Publication No. 2011/0006458, and U.S. Patent Publication No. 2011/0276028, the entire contents of which are explicitly incorporated herein by reference.

FIG. 1 is an image showing an exemplary microstructure array. The microstructures in this array have a basement or proximal layer adjacent the substrate and a distal layer adjacent the proximal layer. Preferably, the distal layer includes at least one therapeutic agent. Preferably, at least a portion of the microstructure separates, detaches, is severed, fractures, shatters or breaks from the array after the microstructure array is applied to skin to remain in the skin after the substrate and any remaining microstructure is removed from the skin.

Figure 2A:
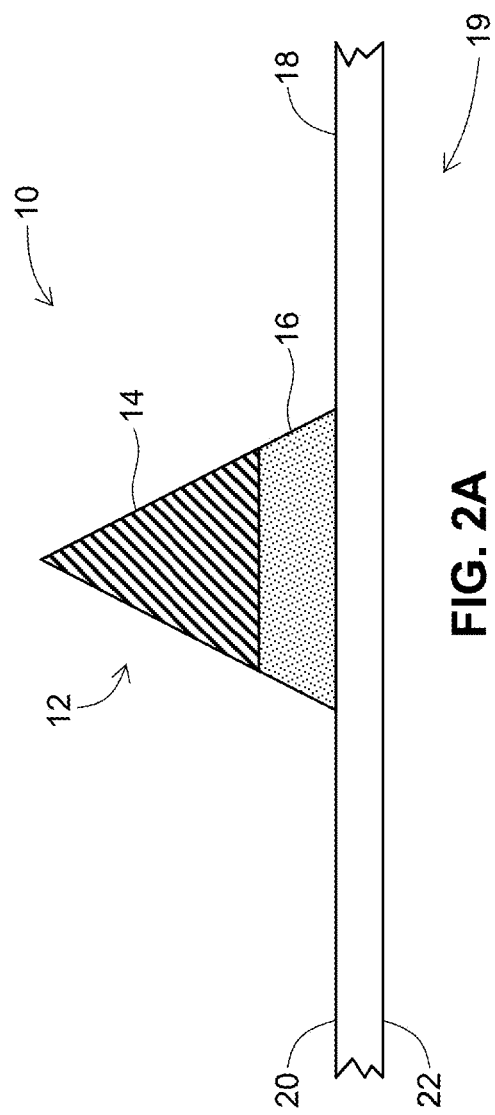

FIGS. 2A-2B illustrates an exemplary microstructure array 10 showing a microstructure 12 with a distal layer 14 and a proximal layer 16. In these embodiments, the microstructure is typically characterized as comprising at least one drug-in-tip (DIT) layer 14 and at least one proximal layer 16. It will be appreciated that any number of intermediate layers may be included between the distal layer 14 and the proximal layer 16. The microstructures 12 are typically positioned on a base, substrate or backing layer 18 having a first surface 20 and a second surface 22 to form the array 10. The microstructures may be attached to the substrate by any suitable means. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax. It will be appreciated that any medical device adhesive known in the art would be suitable. In another embodiment, at least a portion of the microstructures are integral with the substrate. It will be appreciated that the substrate or backing layer may include all or a portion of the proximal layer. In the embodiment where the substrate or backing layer comprises all of the proximal layer, the microstructure may comprise an additional layer between the substrate/backing layer and the distal layer or the distal layer may adjoin the portion of the substrate/backing layer that forms the proximal portion of the microstructure. As seen in FIGS. 2A-2B, the microstructures typically extend upwardly at an angle from the substrate. In a preferred embodiment, the microstructures extend substantially perpendicular to the substrate. FIG. 2B illustrates an exemplary microstructure array 10 extending outwardly from the first surface 20 of a backing 18, and a substrate 21 having a first surface 23 and a second surface 25 opposed thereto, where the second surface 22 of the backing is affixed to the first surface 23 of the substrate.

The substrate and/or backing layer 18 is typically formed of one or more biocompatible and/or non-biodegradable materials. The substrate and/or backing layer may be formed of any suitable material that provides the necessary support for the microstructures. Preferably, the substrate and/or backing layer is formed of a synthetic or natural material that is biocompatible at least on the surface that may contact the patient's skin 19. Suitable materials include, but are not limited to, metals, silicon and/or polymers. Suitable metals include, but are not limited to titanium, tantalum, alloys such as stainless steel and cobalt-chromium alloys, or combinations thereof. In an embodiment, the substrate and/or backing layer comprises one or more polymer. In an embodiment, the substrate and/or backing layer comprises one or more water insoluble polymers. Suitable polymers include, but are not limited to, polyethylene terephthalate and polyether ether ketone, polycarbonate, polyethylene, or other film forming polymers. Further suitable polymers are described in U.S. Pat. No. 7,785,301, which is incorporated herein in its entirety. The substrate and/or backing layer may be rigid, substantially rigid or may be at least partially flexible to conform to the surface of the patient's skin. In any case, the substrate and/or backing layer should be sufficiently strong and/or rigid to assist in or allow for the microstructures to at least partially penetrate the patient's skin. The substrate and/or backing layer is typically substantially planar, but may be contoured.

In reference to the microstructures themselves, in general, at least a portion of the microstructures have a height above the base or structure that is sufficient to pierce at least a portion of the epidermis. In embodiments, the microstructures have a height sufficient to pierce all or a portion of the stratum corneum. Typically, the microstructures have a height that penetrates into the epidermis where the density of nerve receptors are low. In embodiments, at least a portion of the microstructures have a height of at least about 50 µm or at least about 100 µm, or at least about 150 µm, or at least about 200 µm, or at least about 250 µm, or at least about 300 µm. In general, the microstructures have a height of no more than about 1 mm, no more than about 500 µm, no more than about 300 µm, no more than about 200 µm, or no more than about 150 µm. In embodiments, the microstructures have a height of between about 50 µm-1 mm. It will be appreciated that the microstructures within an array may have different heights. The microstructures may have an aspect ratio (height to diameter at base) of at least 10:1, preferably at least about 5:1, more preferably at least about 3:1, or at least about 2:1, or at least about 1:1. As the depth of the epidermis and/or dermis layers may be different depending on the area of the body, it will be appreciated that the height of the microstructures may be adjusted depending on the administration site.

One illustrative shape for the microstructures is a cone with a polygonal bottom, for example, being hexagonal or rhombus-shaped. Additional microstructure shapes include those provided, for example, in U.S. Patent Publication No. 2004/0087992. In embodiments, at least a portion of the microstructure shape may be substantially cylindrical, cone-shaped, funnel-shaped, or pyramidal. In further embodiments, at least a portion of the microstructures has an asymmetrical cross-dimensional shape. Suitable asymmetric shapes include, but are not limited to, rectangular, square, oval, elliptical, circular, rhombus, triangular, polygonal, star-shaped, etc. In some embodiments, the distal layer has a cross-dimension in one direction that is smaller than the cross-dimension in the other direction. Exemplary cross-dimensional shapes with this configuration include, but are not limited to, rectangular, rhombus shaped, ellipse, and oval. In non-limiting embodiments, the base of the microstructure distal layer has a cross-dimensional distance that is less than about 100 µm. In other embodiments, the base of the distal layer has a cross-dimensional distance that is less than about 70 µm. In yet other embodiments, the base of the distal layer has a cross-dimensional diameter that is less than about 50 µm. In further embodiments, the base of the distal layer has a cross-dimensional diameter that is less than about 50-100 µm, less than about 50-70 µm, or less than about 70-100 µm. It will be appreciated that the cross-dimensional shape may be varied along the length of the microstructure. The distal tip has a diameter <1 micron, or <5 microns, or <10 microns. It will further be appreciated that different portions and/or layers of a microstructure may have different cross-dimensional shapes. At least a portion of the microstructures may include one or more blade or piercing elements along its length and/or at the distal tip.

Figure 8A:
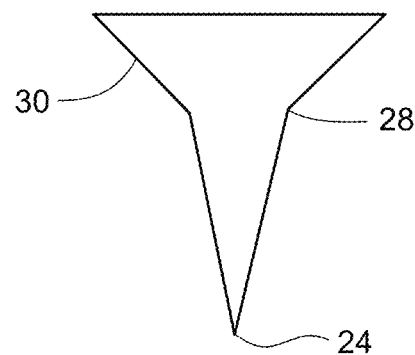
FIGS. 8A-8B are illustrations of exemplary shapes for microstructures including a funnel shape.
Figure 8B:
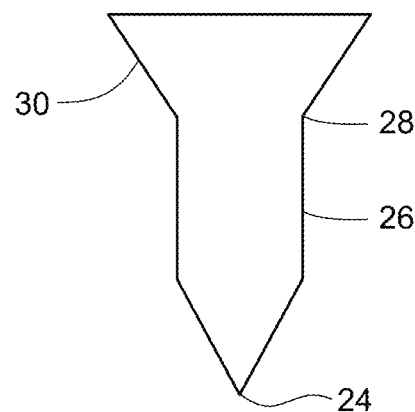

Microstructure shape can be understood in terms of a tip, a shank and a funnel. The angle at the tip is the apex angle—included angle by the planes or cone—and can have values from about 5 degree to about 60 degrees. The straight or substantially straight shank may or may not be present in a particular microstructure design. At the base of the shank or tip, towards the distal end, the included angle has a discontinuity or a point of inflection. The included angle jumps to take on a value greater than the apex angle for a shank-less tip and to greater than 0 degrees for microstructures with a shank. Portions of the microstructure beyond this point of inflection may be referred to as a "funnel". FIGS. 8A and 8B show examples of cross sectional elevation of the microstructures delineating different regions including the tip 24, shank 26, inflection point or edge 28 and the funnel 30. In FIG. 8B, the diameter of the microstructure is growing faster than linear fashion with respect to the distance from the distal end. Where microstructures are thicker towards the base, a portion of the microstructure adjacent to the base, which may be referred to herein as a "proximal portion" "backing portion", "basement" or "foundation" or as an "upper portion" may be designed not to penetrate the skin.

As described in Example 4, the proximal funnel shape allows for relatively larger volumes to be dispensed in the microstructure mold for a given total length of the microstructure. The proximal funnel shape provides a larger volume (to fill) without requiring a proportional increase in microstructure height, which results in a longer drug containing portion in the microstructure. Thus, the proximal funnel shape allows for a larger solid volume for the distal portion of the microstructure with a single fill of the mold. Other shapes may require several fill and dry cycles to achieve the same amount of solid distal portion as one fill and dry cycle for the funnel shaped microstructures.

Figure 6:
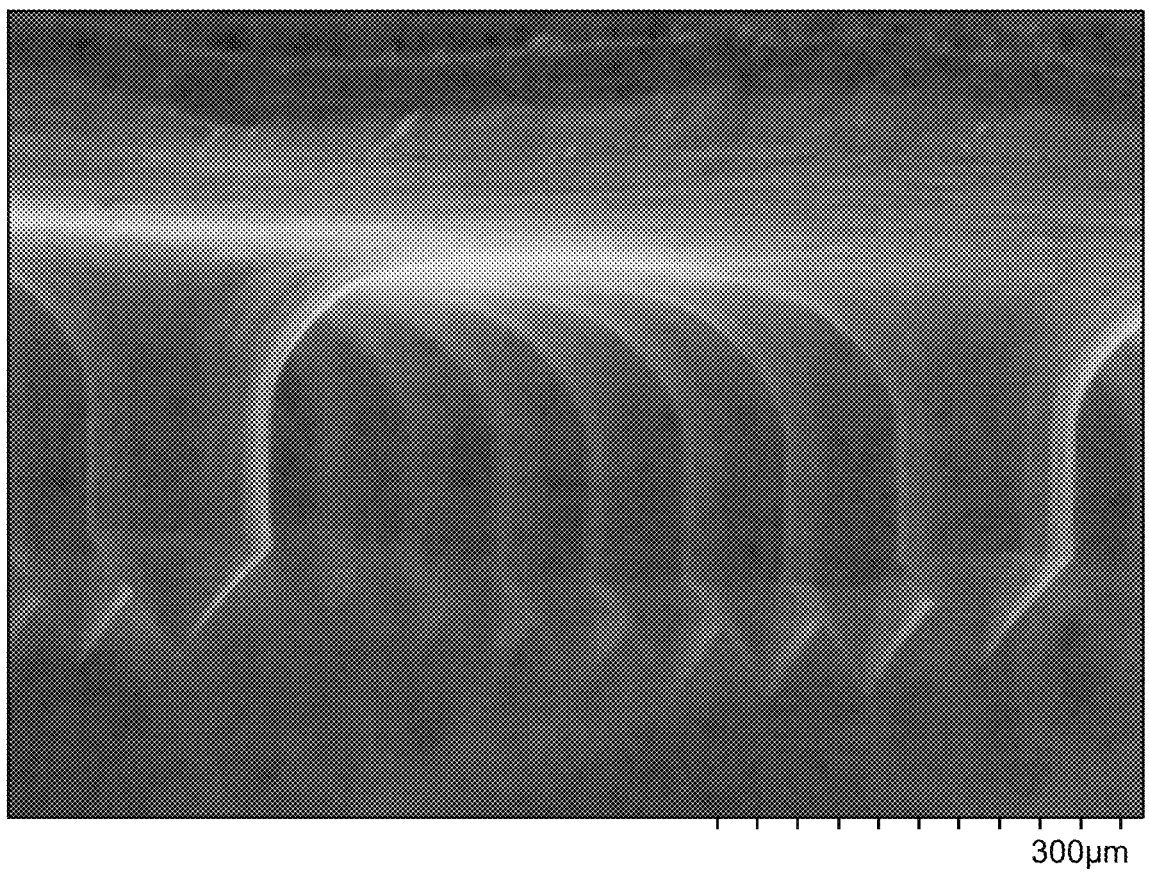
FIG. 6 is a microscopic image of a microstructure array where the microstructures have a cylindrical funnel shape.
Figure 7A:
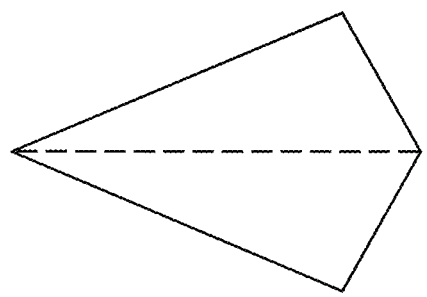
FIGS. 7A-7C are illustrations of exemplary shapes for microstructures of the arrays described herein.
Figure 7B:
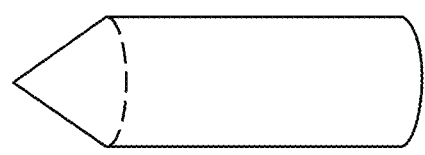
Figure 7C:
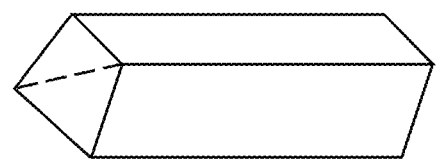

In one exemplary embodiment, at least a portion of the microstructures have a cylindrical funnel shape as shown in the array of FIG. 6. As seen in the image, microstructures with this shape have a cylindrical shank and a funnel at the proximal end. In this embodiment, the distal tips of the microstructures typically, but not always, have a sharp, pointed or conical distal end to ease and/or facilitate penetration. The microstructures further have a funnel shape at the proximal end and a cylindrical shank between the distal and proximal ends.

The funnel shape offers several advantages including a reduction in pinning (liquid formulation adhering or sticking to the mold sides) during manufacturing.

The funnel portion may also be used to limit the depth of penetration. Since the funnel has a several times higher volume per unit height than the tip or shank, it also requires several times higher energy to penetrate per unit depth than the tip or shank. Hence for a given energy, the microstructure would typically penetrate no more than the length of the tip and shank. The funnel thus effectively acts as the design element in the microstructure that limits the depth of penetration thereby ensuring tolerable sensation. Generally, the number of microstructures in the array is preferably at least about 50, at least about 100, at least about 500, at least about 1000, at least about 1400, at least about 1600, or at least about 2000. For example, the number of microstructures in the array may range from about 1000 to about 4000, or from about 2000 to about 4000, or from about 2000 to about 3500, or from about 2200 to about 3200. The area density of microstructures, given their small size, may not be particularly high, but for example the number of microstructures per $cm^2$ may be at least about 50, at least about 250, at least about 500, at least about 750, at least about 1000, at least about 2000, or at least about 3000.

While the array itself may possess any of a number of shapes, the array is generally sized to possess a diameter of from about 5 millimeters to about 25 millimeters, or from about 7 to about 20 millimeters, or from about 8 to about 16 millimeters. Exemplary diameters include 5, 6, 7, 8, 9, 10, 11, 12, 13, 14, 15, 16, 17, 18, 19, 20, 21, 22, 23, 24, and 25 millimeters.

In a preferred embodiment, at least the distal layer of at least a portion of the microstructures is formed of a biodegradable, bioerodible, bioabsorbable and/or biocompatible polymer matrix. Biocompatible, biodegradable, bioabsorbable and/or bioerodible polymers for use in the instant microprojection arrays include, but are not limited to, poly (lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), other polysaccharides, polyalcohols, gelatin, alginate, chitosan, hyaluronic acid and its derivatives, collagen and its derivatives, polyurethanes, and copolymers and blends of these polymers. A preferred hydroxyethyl starch has a degree of substitution of in the range of 0-0.9.

The biodegradability or dissolvability of the microprojection array may be facilitated by the inclusion of sugars. Exemplary sugars include dextrose, fructose, galactose, maltose, maltulose, iso-maltulose, mannose, lactose, lactulose, sucrose, and trehalose. Sugar alcohols, for example lactitol, maltitol, sorbitol, and mannitol, may also be employed. Cyclodextrins can also be used advantageously in microneedle arrays, for example α, β, and γ cyclodextrins, for example hydroxypropyl-β-cyclodextrin and methyl-β-cyclodextrin. Sugars and sugar alcohols may also be helpful in stabilization of peptides and proteins and in modifying the mechanical properties of the microprojections by exhibiting a plasticizing-like effect.

The polymers used may possess a variety and range of molecular weights. The polymers may, for example, have molecular weights of at least about 1K Da, at least about 5K Da, at least about 10K Da, at least about 20K Da, at least about 30K Da, at least about 50K Da, or at least about 100K Da. Where the microstructure is meant to be biodegradable, it may be desired to have biodegradable portion(s) comprise one or more polymers having a lower molecular weight. The strength-molecular weight relation in polymers is an inverse relation so polymers with lower molecular weights have a lower strength and will tend to be more biodegradable. Further polymers with a lower molecular weight will be more likely to break due to the lower strength. In one embodiment, at least the distal layer comprises at least one polymer having a lower molecular weight. In an embodiment, at least the distal layer comprises at least one polymer having a molecular weight less than about 100K Da. In another embodiment, at least the distal layer comprises at least one polymer having a molecular weight less than about 20K Da. In other embodiments, at least the distal layer comprises at least one polymer having a molecular weight less than about 1K Da, less than about 5K Da, less than about 10K Da, less than about 15K Da or less than about 20K Da. In one embodiment, at least the distal layer comprises at least one polymer having a molecular weight of between about 1K-100K Da or between about 1K-20K Da. In other embodiments, the distal layer comprises at least one polymer having a molecular weight of between about 1K-100K Da, between about 1000-5000 Da, between about 1000-10,000 Da, between about 1000-15,000 Da, between about 5000-10,000 Da, between about 5000-15,000 Da, between about 5000-20,000 Da, between about 10,000-15,000 Da, between about 10,000-20,000 Da, and between about 15,000-20,000 Da. It will be appreciated that the distal layer may comprise one or more polymers having a lower molecular weight while the proximal layer and/or the substrate may comprise polymers having a higher molecular weight. It will be appreciated that the polymers for the distal and/or proximal portions may be selected based at least partly on the molecular weight of the polymers to facilitate separation or detachment of at least a portion of the microstructures.

In other embodiments, at least the distal layer comprises at least one hydrophobic polymer. In one embodiment, the distal layer is formed of a polymer matrix comprising one or more hydrophobic polymers, with or without hydrophilic polymers. Hydrophilic polymers tend to take up water to swell and weaken the strength of the distal layer, thus make it easier to detach. Hydrophobic polymers will be less prone to take up any water and would therefore remain brittle, if initially brittle. These brittle polymers are easier to break. In one embodiment, the polymer matrix comprises 1-100% hydrophobic polymer(s) and 0-99% hydrophilic polymer(s). In other embodiments, the polymer matrix comprises 50-100% hydrophobic polymer(s) and 0-50% of hydrophilic polymer(s). In yet another embodiment, the polymer matrix comprises 80-100% hydrophobic polymer(s) and 0-20% hydrophilic polymer(s). It will be appreciated that the hydrophobic and/or hydrophilic polymer portions of the matrix may comprise one or more polymers. Suitable hydrophobic and/or hydrophilic polymers are known in the art. Exemplary hydrophobic polymers include, but are not limited to, PLA, α-hydroxy acids such as PLGA, polycaprolactones, and polyanhydrides. It will be appreciated that the hydrophobic and/or hydrophilic polymers may be selected to achieve a desired degradation rate. Further, the polymers may be co-polymerized to achieve a desired degradation rate. For co-polymers, it will further be appreciated that the ratio of the monomers may be adjusted to achieve a desired hydrophobicity/hydrophilicity and/or degradation rate. For example, lactide rich PLGA copolymers are more hydrophobic than glycolide rich PLGA copolymers. Additionally, the ratio of hydrophobic:hydrophilic polymer in the matrix may be selected to achieve the desired degradation rate. It will be appreciated that the choice of polymer and/or ratio may be used to achieve a desired brittleness to facilitate separation or detachment of the microstructures.

Certain semi-crystalline as well as amorphous polymers exhibit a glass transition temperature (Tg). The Tg of a polymer is the temperature where the polymer transitions from a hard, glass-like state that is relatively brittle to rubber-like state. Polymers that are in the glass state are easier to break. Thus, it may be desirable to select polymers for portions of the microstructures that are below the Tg during use. In one embodiment, at least a portion of the microstructures is formed of at least one polymer that is in a glass state at room temperature. In another embodiment, at least the proximal layer and/or distal layer of the microstructures is formed of a polymer matrix that is in a glass state at room temperature (typically between about 16° C.-30° C., preferably between about 20° C.-25° C.). In other embodiments, at least the proximal layer and/or the distal layer of the microstructures is formed of a polymer matrix that is in a glass state at body temperature, typically core body temperature (about 98.6° F.±1°). This results in the proximal layer and/or the distal layer being relatively brittle during use and thus more prone to detach or break from the array. Thus, the detachment area may be controlled by forming the layer for detachment of a polymer matrix that is in a glass state at a desired temperature. In non-limiting embodiments, at least a portion of the microstructures are formed of at least one polymer having a Tg at or above room temperature. In embodiments, the at least one polymer has a Tg at or above about 20° C. In further embodiments, the at least one polymer has a Tg at or above about 20°-25° C. In other embodiments, at least a portion of the microstructures is formed of at least one polymer having a Tg at or above about normal body temperature. In one embodiment, at least a portion of the microstructures is formed of at least one polymer having a Tg at or above about 37° C.±2° C. In embodiments, the at least one polymer has a Tg at or above about 35° C.-38° C. In further embodiments, at least a portion of the microstructures is formed of at least one polymer having a Tg at least about 5°-10° above body temperature. In embodiments, at least a portion of the at least one polymer has a Tg at least about 5° C., at least about 10° C., or at least about 15° C. above about 35° C. In other embodiments, at least a portion of the microstructures comprise a polymer matrix having one or more of the above Tg. Methods for determining the Tg of a polymer are well known in the art and include, but are not limited to, differential scanning calorimetry (DSC) and thermomechanical analysis (TMA).

Preferably, at least a portion of the distal layer comprises a polymer matrix and at least one therapeutic agent, active agent, or drug (collectively "agent" hereafter). The agent to be administered can be one or more of any of therapeutic agents, active agents or drugs known in the art, and include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine;

nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof. In some embodiments, the agent is a protein or a peptide. In other embodiments, the agent is a vaccine.

Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and include DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. Examples of vaccines include, but are not limited to, vaccines to varicella, diphtheria, pertussis, hepatitis (A and/or B), Human Papillomavirus, influenza, measles, mumps, rubella, whooping cough, polio, tetanus, meningitis, shingles, etc.

In another embodiment, at least a portion of the distal layer comprises an agent suitable for veterinary uses. Such uses include, but are not limited to, therapeutic and diagnostic veterinary uses.

It will be appreciated that addition of a drug in the polymer matrix may affect the Tg of the polymer(s) and/or matrix. The amount of drug in the matrix may be selected to achieve a desired Tg and/or resulting brittleness/elasticity for the matrix. The agent may act as a plasticizer when added to the matrix resulting in a decrease of the matrix Tg and weaken the strength of microstructures. Further, the amount of agent loaded in the matrix may affect the Tg and/or the brittleness/elasticity of the polymer matrix.

In one embodiment, the agent is a small molecule drug. In non-limiting embodiments, the polymer matrix comprises at least about 1-99% of one or more small molecule drugs that are at least partially soluble with the at least one polymer in a solvent or co-solvent. In other embodiments, drug loading is at least about 5-50% of the drug, at least about 5-40% of the drug or at least about 10-30% of the drug in the matrix. Agents that are not soluble with the at least one polymer in a solvent or co-solvent may be added in particle form and suspended or dispersed in the matrix. This formulation will work at least for large molecular drugs such as proteins and peptides. For a suspension or dispersion, the drug load in the matrix is generally, but not limited to, at least about 1-99%, at least about 1-90%, at least about 5-50%, preferably at least about 10-40% or at least about 20-30%.

It will be appreciated that the microstructures may comprise one or more agents in each layer. It will further be appreciated that at least a portion of the microstructures may include a coating that may contain one or more agents.

In other embodiments, the at least one polymer is included in the matrix at a concentration that is lower than or close to the entanglement concentration ($C_E$) for the polymer. The entanglement concentration is the concentration of the polymer in the matrix where polymer chains interwind and become entangled. The entangled polymer chains decrease the ability of the polymers to move within the matrix, thus, decreasing the ability of a portion of the microstructure to detach or break. The $C_E$ is dependent upon molecular weight as the longer chains overlap and then entangle at lower concentrations. Conversely, polymers with a lower molecular weight have a higher $C_E$. In an embodiment, a concentration of at least one polymer in a polymer casting solution used to prepare the microstructures is at or below the $C_E$ for that polymer The $C_E$ can be determined by e.g. viscosity measurement of polymer solution. By double logarithm plot of viscosity against polymer concentration, the transition point from one slope to another slope is estimated as entanglement concentration.

As further seen in FIG. 2, the microstructure includes one or more proximal layers 16. The proximal layer is preferably attached to or affixed to or integral with the first surface of the substrate and the distal layer. It will be appreciated that where the microstructure includes one or more intermediate layers as discussed below, the proximal layer is attached to, affixed to, or integral with the first surface of the substrate and the adjoining intermediate layer. The proximal layer is typically biocompatible. The proximal layer may comprise one or more biodegradable and/or non-biodegradable polymers. Suitable biodegradable polymers are described with reference to the distal layer. Suitable non-biodegradable polymers are known in the art and include, but are not limited to, amphiphilic polyurethanes, polyether polyurethane (PEU), polyetheretherketone (PEEK), and polyamide-imide (PAI). In another embodiment, the proximal layer is an adhesive layer. One suitable adhesive is the Dymax® 1187-M UV medical device adhesive. It will be appreciated that any biocompatible adhesive is suitable for use with, in and/or as the proximal layer. This layer may also be a nonwoven or porous film double coated with pressure sensitive adhesive.

It will be appreciated that one or more layers may be included between the proximal 16 and distal 14 layers. These intermediate layers may comprise a biodegradable or non-biodegradable matrix. The intermediate layers may be formulated to promote detachment of the distal layer(s). Biodegradable intermediate layers may contain one or more agents that are the same as or different than the agent in the distal layer. In one embodiment, the intermediate layers comprise an agent that is different than the agent in the distal layer. In another embodiment, the intermediate layers comprise an adjuvant or other agent that modifies or modulates the action of the agent in the distal layer. In one non-limiting example, the distal layer may comprise a vaccine while the intermediate layer comprises an adjuvant for the vaccine. In a further embodiment, the intermediate layers comprise the same agent as in the distal layer. In this embodiment, the agent may be present at a different dose (higher or lower) than present in the distal layer. Further, the intermediate layer may degrade at a faster or slower rate than the distal layer. For example, the distal layer may degrade rapidly (e.g. minutes to hours) providing an initial dose of the agent while the intermediate layer degrades more slowly (e.g. hours to days, weeks, or months) providing sustained release of the agent. An intermediate layer may also be used to control separation or detachment of the microstructures. For example, an intermediate layer may be formulated to promote detachment to ensure the entire distal layer is deployed into the patient's skin.

Preferably, at least a portion of the microstructure detaches or breaks off after the microstructure is inserted into tissue and remains in the skin until degraded or removed by normal processes. Preferably, at least a portion of the distal layer detaches from the microstructure after it is inserted into skin. The distal layer may detach at a point within the distal layer or the distal layer may detach at the intersection or joint of the distal layer and the proximal layer. In other embodiments, the microstructure detaches at or near an intermediate layer positioned between the distal layer and the proximal layer. The detachment point is not critical as long as enough agent is contained within the detached portion to be effective for treatment. In one embodiment, at least about 10% of the distal layer detaches from the microstructure. In further embodiments, at least about 25%, at least about 50%, at least about 70%, at least about 75%, at least about 80%, at least about 90%, at least about 95%, at least about 99%, or at least about 100% of the distal layer detaches from the microstructure. In other embodiments, at least about 10-100% of the distal layer detaches from the microstructure. In additional embodiments, at least about 15-100%, at least about 25-100, at least about 30-100%, at least about 40-100%, at least about 50-100%, at least about 60-100%, at least about 70-100%, at least about 75-100%, at least about 80-100%, at least about 90-100%, at least about 95-100%, or at least about 99-100% of the distal layer detaches from the microstructure. In one embodiment, the distal tip detaches below the surface of the skin. This ensures that the entire detached tip degrades into the skin thereby releasing all, substantially all, or most of the agent in the matrix into the skin. Having the distal tip detach below the skin surface may also allow skin to close over the top of the embedded tip, which promotes healing of the insertion area and prevents the microstructure from extending out from the skin, which may be irritating to the patient.

At least a portion of the microstructures detach readily upon insertion of the array into skin or shortly thereafter. In a non-limiting embodiment, the microstructures detach within about 10 seconds to about 10 or 15 minutes after insertion. In embodiments, the microstructures detach within about 1-10 minutes, about 2-10 minutes, about 3-10 minutes, about 4-10 minutes, about 5-10 minutes, about 6-10 minutes, about 7-10 minutes, about 8-10 minutes, about 9-10 minutes, about 30 seconds to about 6 minutes, about 1-6 minutes, about 2-6 minutes, about 3-6 minutes, about 4-6 minutes, about 5-6 minutes, about 30 seconds to about 5 minutes, about 1-5 minutes, about 2-5 minutes, about 3-5 minutes, about 4-5 minutes, about 30 seconds to about 4 minutes, about 1-4 minutes, about 2-4 minutes, about 3-4 minutes, about 30 seconds to about 3 minutes, about 1-3 minutes, about 2-3 minutes, about 30 seconds to about 2 minutes, or about 1-2 minutes. In other embodiments, the microstructures detach within at least about or less than about 10 seconds, about 30 seconds, about 1 minute, about 90 seconds, about 2 minutes, about 3 minutes, about 4 minutes, about 5 minutes, about 6 minutes, about 7 minutes, about 8 minutes, about 9 minutes, about 10 minutes, or about 15 minutes.

In non-limiting embodiments, detachment of the microstructure occurs at a time before or faster than all or a portion of the distal tip degrades. In this embodiment, the microstructures are inserted into the skin and at least a portion of the microstructures detach from the array. The detached microstructure portions degrade or continue to degrade within the skin. In embodiments, detachment of the microstructure occurs at a time before or faster than a majority of the distal tip degrades. In embodiments, the microstructure detaches at least about 10 seconds to about 10 minutes before the distal tip degrades. In embodiments, the microstructures detach about 30 seconds to about 10 minutes, about 1-10 minutes, about 2-10 minutes, about 3-10 minutes, about 4-10 minutes, about 5-10 minutes, about 6-10 minutes, about 7-10 minutes, about 8-10 minutes, about 9-10 minutes, about 30 seconds to about 6 minutes, about 1-6 minutes, about 2-6 minutes, about 3-6 minutes, about 4-6 minutes, about 5-6 minutes, about 30 seconds to about 5 minutes, about 1-5 minutes, about 2-5 minutes, about 3-5 minutes, about 4-5 minutes, about 30 seconds to about 4 minutes, about 1-4 minutes, about 2-4 minutes, about 3-4 minutes, about 30 seconds to about 3 minutes, about 1-3 minutes, about 2-3 minutes, about 30 seconds to about 2 minutes, or about 1-2 minutes before the distal tip degrades. In other embodiments, the microstructures detach at least about 10 seconds, about 30 seconds, about 1 minute, about 90 seconds, about 2 minutes, about 3 minutes, about 4 minutes, about 5 minutes, about 6 minutes, about 7 minutes, about 8 minutes, about 9 minutes, about 10 minutes, or about 15 minutes before the distal tip degrades, or a portion or a majority thereof.

In embodiments at least about 10-100% of at least a portion of the microstructures readily detach. In specific non-limiting embodiments, at least about 10-99%, about 10-95%, about 10-90%, about 10-85%, about 10-80%, about 10-75%, about 10-70%, about 10-65%, about 10-60%, about 10-50%, about 10-40%, about 10-30%, about 30-99%, about 30-95%, about 30-90%, about 30-85%, about 30-80%, about 30-75%, about 30-70%, about 30-65%, about 30-60%, about 30-50%, about 30-40%, about 40-99%, about 40-95%, about 40-90%, about 40-85%, about 40-80%, about 40-75%, about 40-70%, about 40-65%, about 40-60%, about 40-50%, about 50-99%, about 50-95%, about 50-90%, about 50-85%, about 50-80%, about 50-75%, about 50-70%, about 50-65%, about 50-60%, about 60-99%, about 60-95%, about 60-90%, about 60-85%, about 60-80%, about 60-75%, about 60-70%, about 60-65%, about 65-99%, about 65-95%, about 65-90%, about 65-85%, about 65-80%, about 65-75%, about 65-70%, about 70-99%, about 70-95%, about 70-90%, about 70-85%, about 70-80%, about 70-75%, about 85-99%, about 85-95%, about 85-90%, about 90-99%, about 90-95%, or about 95-99%. In other embodiments, at least about 10%, about 20%, about 30%, about 40%, about 50%, about 60%, about 65%, about 70%, about 75%, about 80%, about 85%, about 90%, about 95%, about 99%, or about 100% of at least a portion of the microstructures detach.

The microstructures may be fabricated such that all or a portion of the microstructures break off or dissolve off of the proximal layer, substrate or backing, or intermediate layer after insertion into skin. In an embodiment, the microstructure may be formed of a homogeneous material in which the material is more readily degradable at lower pH's as described in U.S. Patent Application No. 2009/0155330. In other embodiments, at least the distal tip may include a bioadhesive material or polymer that promotes adhesion to the interior skin adjacent the inserted microstructure. Thus, the bioadhesive facilitates detachment of the distal layer. In other embodiments, the microstructure may be etched, notched or scored to promote detachment as well as to promote detachment at a particular area of the microstructure.

The microstructures may further be shaped or formulated to promote detachment of all or a portion of the microstructures after insertion. The microstructure shape and content may be designed to promote and/or control detachment of at least a portion of the microstructure. For example, the microstructures may be formulated to soften or dissolve at certain points as described in U.S. Patent Publication No. 2009/0043279. Further, polymer(s) may be chosen for inclusion in one or more layers to promote detachment of that or other layers. For example, hydrophobic polymers, polymers having a high Tg, and/or polymers with a low molecular weight may be chosen to promote detachment. The composition of the layer may, alone or in addition to the polymer choices, be adjusted or manipulated to promote detachment of all or a portion of the microstructures. For example, the percentage of drug in the polymer matrix and/or the use of polymers at or near the entanglement concentration in the matrix may promote detachment. Further, the microstructure shape may be designed or manipulated to promote detachment. Examples include having a shape with an asymmetrical cross-sectional diameter. It will be appreciated that the microstructures may be formulated with one or more, or all of the features as discussed above including adjusting the percentage of drug in the polymer layer, including polymers with a high Tg, using polymers with a lower molecular weight, including polymers in the matrix at or below the entanglement concentration, using hydrophobic polymers, and/or designing the shape of the microstructures.

All or a portion of the microstructures may include an indicator to provide visual verification of insertion and detachment of the microstructures in the skin as described in U.S. Patent Publication No. 2012/0150023. The indicator is preferably biocompatible as it will typically be delivered into the skin as the microstructure degrades.

III Methods of Making Microstructure Arrays

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

Examples of forming various microstructure arrays having different configurations are provided in Examples 1 and 4. In one exemplary method, an array is prepared by (a) filling a mold with cavities corresponding to the negative of the microstructures with a casting solution comprising a biocompatible material such as a biocompatible polymer and a solvent, (b) removing the solvent, and (c) de-molding the resulting array from the mold. The solvent may be removed by any suitable means including, but not limited to, drying the mold filled with the casting solution in an oven. The casting solution preferably contains an active agent or ingredient. In one or more embodiments, the microstructures themselves comprise the active ingredient mixed, or dispersed in a polymer matrix, as opposed to having the active ingredient present as a coating on a microstructure or microneedle made of a different, biocompatible material such as a metal. Typically, excess formulation is scraped or wiped from the mold surface prior to drying. Where the microstructures are not integral with a substrate or backing layer, the microstructures are affixed to the substrate or backing layer with an adhesive prior to de-molding.

IV. Methods of Use

The methods, kits, microstructure arrays and related devices described herein may be used for treating any condition. It will be appreciated that the microstructure arrays may be used with any appropriate applicator including the applicator described in U.S. patent application Ser. No. 13/100,924, now published as U.S. Publication No. 2011/0276027 filed on May 4, 2011, which is incorporated herein in its entirety.

V. Examples

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Casting Two-Layer Arrays

Clonidine was dissolved in an acetonitrile (ACN)/DMSO (7/3, v/v) mixture to a concentration of 35% (w/w) to form a drug solution.

Poly(D,L-lactide-co-glycolide) (PLGA, UG 75/25) (available from Durect Corporation (PN B6007-1P), IV 0.55-0.75) and PLGA (L/G 75/25) from SurModics (1A, IV 0.1) was dissolved in ACN to a concentration of 40% to form a polymer solution.

The liquid drug formulation was prepared by mixing the drug solution with the polymer solution.

About 75 μL of liquid drug formulation was dispensed on a silicone mold, covered with 22 mm×30 mm glass cover slip to spread the formulation on the mold, and then pressurized at 50 psi for 1 minute.

The formulation was wiped and the mold dried in an oven at 32° C. for about half an hour.

UV adhesive was dispensed on the drug formulation in the mold, covered with a 5 mL polyethylene terephthalate (PET) or polycarbonate (PC) film to spread the adhesive and cured using a UV Fusion system. The UV curing dose was 1.6 J/cm$^2$. After curing, the microstructure (drug in tip distal layer and UV adhesive proximal layer on PET) was die cut with an 11 or 16 mm punch.

The resulting microstructures were inspected under microscope.

Example 2

Administration of a Microstructure Array

A microstructure array comprising a therapeutic agent is prepared in accord with Example 1. The microstructure array is applied to skin and a force suitable to insert at least a portion of the microstructures into skin is applied to the second surface of the substrate. The microstructure array is removed from skin after 5 minutes.

Figure 3A:
FIGS. 3A-3B are microscopic images of an exemplary microstructure array before (FIG. 3A) and after (FIG. 3B) application to skin for five minutes.
Figure 3B:
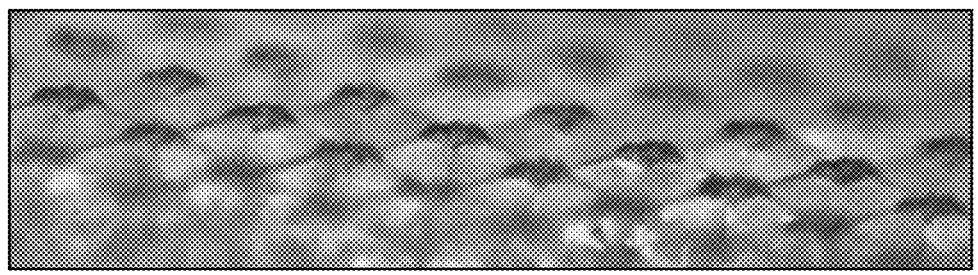
Figure 4:
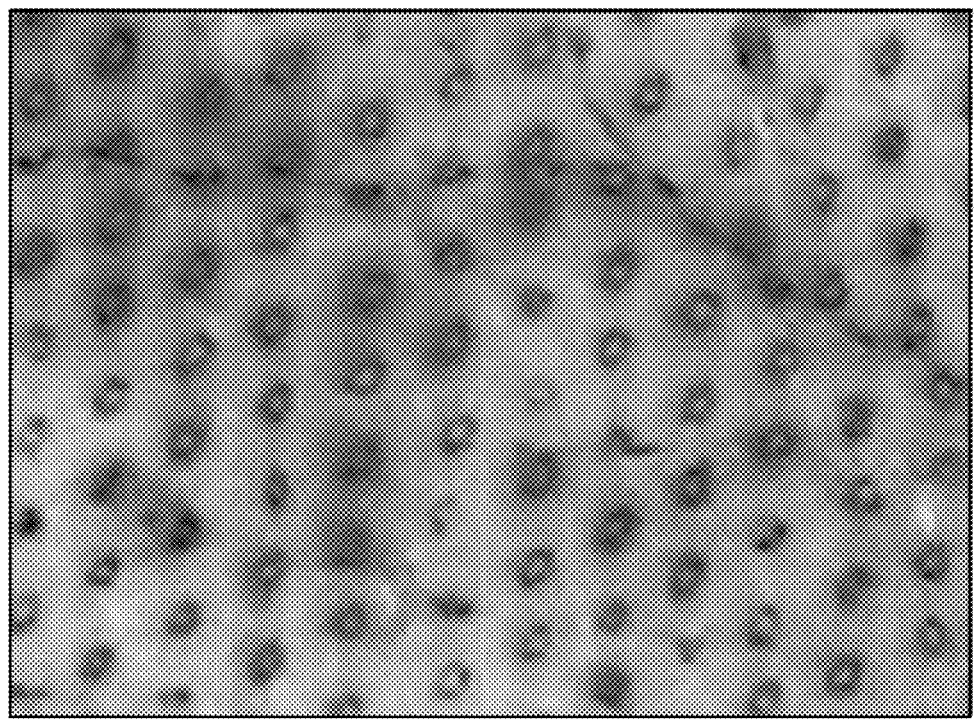
FIG. 4 is a microscopic image of pig skin after application of a microstructure array for five minutes showing the microstructure tips implanted in the skin.
Figure 5A:
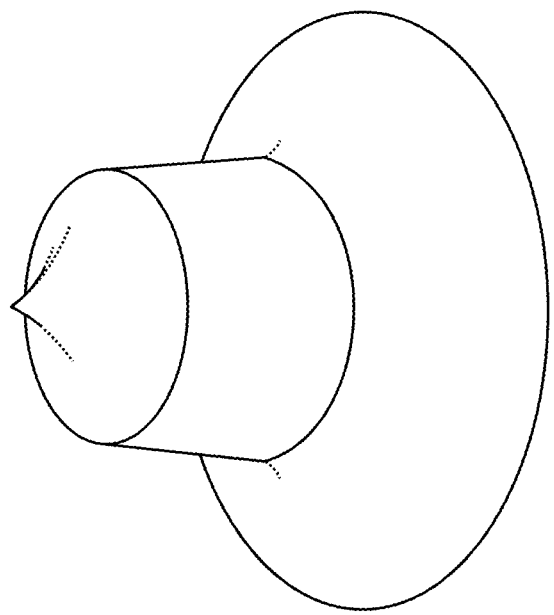
FIGS. 5A-5B are illustrations of an exemplary microstructure having a funnel shape.
Figure 5B:
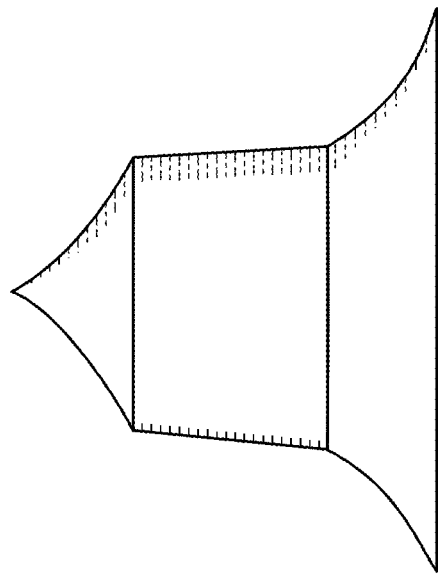

The distal portion of the microstructures detaches from the microstructure array during removal of the array and remain implanted in skin. FIG. 3A shows an exemplary microstructure array before application to skin and FIG. 3B shows the array after application. As seen in FIG. 3B, the distal portions of the microstructures are detached or broken off from the proximal portions of the microstructures. FIG. 4 shows pig skin after application and removal of an exemplary microstructure array. The white dots within the stain are the microstructure distal ends implanted in the skin.

Example 3

Casting Funnel Shaped Microstructure

A liquid drug solution prepared as described in Example 1 is dispensed onto a mold surface having funnel shaped cavities. The filled mold is pressurized to fill the cavities. The mold surface is wiped to remove excess liquid drug solution from the mold. After wiping, the mold with the drug solution is dried. During the drying, a solid dried matrix is formed in the distal microstructure cavities. This dried matrix fills a portion of the distal microstructures depending on the solid content in the liquid drug solution. To load higher doses of drug, the mold cavities will be filled with liquid drug solution as much as possible to achieve the maximum dried solid matrix containing drug. A larger funnel volume results in greater solid matrix after drying, particularly in cylindrical shaped microstructures.

1. A microstructure apparatus comprising:
   a backing having a first surface and a second surface opposed thereto;
   a microstructure array comprising a plurality of microstructures extending outwardly from the first surface of the backing;
   the microstructures comprising a biodegradable distal layer and at least one proximal layer positioned between the distal layer and the first surface of the backing;
   the distal layer comprised of at least one therapeutic agent and at least one polymer; and
   wherein at least a portion of the distal layer detaches readily upon insertion of the array into skin.
2. The microstructure apparatus of embodiment 1, wherein the distal layer comprises at least one hydrophobic polymer.
3. The microstructure apparatus of single or combined embodiments 1 or 2, wherein the distal layer comprises at least one polymer comprises at least one hydrophobic polymer and about 0-99% of at least one hydrophilic polymer.
4. The microstructure apparatus of the single or combined embodiments 1-3, where the distal layer comprises at least one polymer comprises at least one hydrophobic polymer and about 0-50% of a hydrophilic polymer.
5. The microstructure apparatus of the single or combined embodiments 1-4, where the distal layer comprises at least one polymer comprises at least one hydrophobic polymer and about 0-20% of a hydrophilic polymer.
6. The microstructure apparatus of the single or combined embodiments 1-5, where at least one therapeutic agent is a small molecule drug at least partially soluble with the at least one polymer in a solvent or co-solvent.
7. The microstructure apparatus of the single or combined embodiments 1-6, wherein the distal layer comprises about 1-99% of the small molecule drug.
8. The microstructure apparatus of the single or combined embodiments 1-7, wherein the distal layer comprises about 1-50% of the small molecule drug.
9. The microstructure apparatus of the single or combined embodiments 1-8, wherein the distal layer comprises about 5-40% of the small molecule drug.
10. The microstructure apparatus of the single or combined embodiments 1-9, wherein the distal layer comprises about 10-30% of the small molecule drug.
11. The microstructure apparatus of the single or combined embodiments 1-10, where at least one therapeutic agent is dispersed in the distal layer.
12. The microstructure apparatus of the single or combined embodiments 1-11, wherein the distal layer comprises about 1-90% of the dispersed agent.
13. The microstructure apparatus of the single or combined embodiments 1-12, wherein the distal layer comprises about 1-50% of the dispersed agent.
14. The microstructure apparatus of the single or combined embodiments 1-13, wherein the distal layer comprises about 10-40% of the dispersed agent.
15. The microstructure apparatus of the single or combined embodiments 1-14, wherein the distal layer comprises about 20-30% of the dispersed agent.
16. The microstructure apparatus of the single or combined embodiments 1-15, wherein the at least one polymer is in a glass state at room temperature.
17. The microstructure apparatus of the single or combined embodiments 1-16, wherein the at least one polymer has a glass transition temperature (Tg) above about body temperature.
18. The microstructure apparatus of the single or combined embodiments 1-17, where at least about 10% of the distal layer detaches readily upon insertion of the array into skin.
19. The microstructure apparatus of the single or combined embodiments 1-18, where at least about 50% of the distal layer detaches readily upon insertion of the array into skin.
20. The microstructure apparatus of the single or combined embodiments 1-19, where at least about 70% of the distal layer detaches readily upon insertion of the array into skin.
21. The microstructure apparatus of the single or combined embodiments 1-20, where at least about 90% of the distal layer detaches readily upon insertion of the array into skin.
22. The microstructure apparatus of the single or combined embodiments 1-21, where about 100% of the distal layer detaches readily upon insertion of the array into skin.
23. The microstructure apparatus of the single or combined embodiments 1-22, where at least a portion of the microstructures have a first cross-dimensional diameter that is larger than a second cross-dimensional diameter.
24. The microstructure apparatus of the single or combined embodiments 1-23, where at least a portion of the microstructures have a cross-dimensional shape selected from the group consisting of a diamond, a rectangle, and an oval.
25. The microstructure apparatus of the single or combined embodiments 1-24, where at least a portion of the microstructures have an asymmetrical cross-dimensional shape.

26. The microstructure apparatus of the single or combined embodiments 1-25, wherein a concentration of the at least one polymer in a polymer casting solution used to form the microstructures is lower than an entanglement concentration ($C_E$) for the polymer.

27. The microstructure apparatus of the single or combined embodiments 1-26, wherein a concentration of the at least one polymer in a polymer casting solution used to form the microstructures is at a $C_E$ for the polymer.

28. The microstructure apparatus of the single or combined embodiments 1-27, wherein at least a portion of the proximal and/or distal layers has a funnel shape.

29. The microstructure apparatus of the single or combined embodiments 1-28, wherein the microstructures are affixed to the first surface of the backing.

30. The microstructure apparatus of the single or combined embodiments 1-29, wherein at least a portion of the backing forms the proximal layer.

31. The microstructure apparatus of the single or combined embodiments 1-30, further comprising a substrate having a first surface and a second surface opposed thereto, where the second surface of the backing is affixed to the first surface of the substrate.

32. A microstructure apparatus comprising:
a substrate having a first surface and a second surface opposed thereto;
a microstructure array comprising a plurality of microstructures affixed to the first surface of the substrate and extending outwardly therefrom;
the microstructures comprising of a biodegradable distal layer and a proximal layer positioned between the distal layer and the first surface of the substrate;
the distal layer comprised of at least one hydrophobic polymer and at least one therapeutic agent, and
wherein at least a portion of the distal layer detaches readily upon insertion of the array into skin.

33. A microstructure apparatus comprising:
a backing having a first surface and a second surface opposed thereto;
a microstructure array comprising a plurality of microstructures affixed upon the first surface of the backing and extending outwardly therefrom;
the microstructures comprising of a biodegradable distal layer and a proximal layer positioned between the distal layer and the first surface of the backing;
the distal layer comprised of at least one polymer and about 1-90% of a therapeutic agent; and
wherein at least a portion of the distal layer detaches readily upon insertion of the array into skin.

34. A microstructure apparatus comprising:
a backing having a first surface and a second surface opposed thereto;
a microstructure array comprising a plurality of microstructures affixed upon the first surface of the backing and extending outwardly therefrom;
the microstructures comprising a biodegradable distal layer and a proximal layer positioned between the distal layer and the first surface of the backing;
the distal layer comprised of at least one polymer and a therapeutic agent, the at least one polymer having a glass transition temperature (Tg) at least above about body temperature; and
wherein at least a portion of the distal layer detaches readily upon insertion of the array into skin.

35. A microstructure apparatus comprising:
a backing having a first surface and a second surface opposed thereto;
a microstructure array comprising a plurality of microstructures affixed upon the first surface of the backing and extending outwardly therefrom;
the microstructures comprising a biodegradable distal layer and a proximal layer positioned between the distal layer and the first surface of the backing;
the distal layer comprised of at least one polymer having a molecular weight between about 1-100K Da and a therapeutic agent; and
wherein at least a portion of the distal layer detaches readily upon insertion of the array into skin.

36. A microstructure apparatus comprising:
a backing having a first surface and a second surface opposed thereto;
a microstructure array comprising a plurality of microstructures affixed upon the first surface of the backing and extending outwardly therefrom;
the microstructures comprising a biodegradable distal layer and a proximal layer positioned between the distal layer and the first surface of the backing;
the distal layer comprised of at least one polymer and a therapeutic agent; and
wherein at least about 10-100% of the distal layer detaches readily upon insertion of the array into skin.

37. A microstructure apparatus comprising:
a substrate having a first surface and a second surface opposed thereto;
a microstructure array comprising a plurality of microstructures affixed upon the first surface of the substrate and extending outwardly therefrom;
the microstructures comprising a biodegradable distal layer and a proximal layer positioned between the distal layer and the first surface of the substrate;
the distal layer comprised of at least one polymer and a therapeutic agent, the distal layer having a first cross-dimensional diameter that is larger than a second cross-dimensional diameter; and
wherein at least a portion of the distal layer detaches readily upon insertion of the array into skin.

38. The embodiments of the microstructure apparatuses 32-37 in combination with the single or combined embodiments 2-31.

39. A method of making a microstructure apparatus comprising:
dissolving or suspending a therapeutic agent in a solvent to form a therapeutic agent solution or suspension;
dissolving at least one polymer in a solvent to form a polymer solution;
mixing the therapeutic agent solution or suspension and the polymer solution or suspension to form a polymer matrix solution or suspension;
dispensing the polymer matrix solution or suspension on a mold having an array of microstructure cavities; followed by pressurization;
removing excess solution or suspension polymer matrix on the mold surface; and drying the matrix; and
dispensing a basement or backing layer on the mold surface; and
drying the basement or backing layer.

40. The method of embodiment 39, further comprising:
affixing the basement or backing layer to a substrate.

41. The method of the single or combined embodiments 39-40 further comprising:
using a nonwoven or porous film double coated with adhesive to affix the basement or backing layer to a substrate.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A microstructure apparatus comprising:
a backing having a first surface and a second surface opposed thereto;
a microstructure array comprising a plurality of microstructures extending outwardly from the first surface of the backing;
the plurality of microstructures comprising a biodegradable distal layer and at least one proximal layer positioned between the distal layer and the first surface of the backing;
the distal layer comprised of at least one therapeutic agent and a polymer matrix comprising at least one polymer, wherein:
  (i) the at least one polymer is a hydrophobic polymer that is insoluble or substantially insoluble in aqueous solvents, wherein the polymer matrix is comprised of about 50-100% of the hydrophobic polymer, thereby imparting a brittle character to the distal layer and promoting detachment of at least a portion of the distal layer; or
  (ii) the at least one polymer is at a concentration in a polymer casting solution used to form the distal layer of the plurality of microstructures that is at or below an entanglement concentration ($C_E$) for the at least one polymer, thereby promoting detachment of at least a portion of the distal layer; and
wherein the distal layer formed from the polymer matrix having the configuration of (i) or (ii) is configured such that at least the portion of the distal layer detaches from the plurality of microstructures upon insertion of the microstructure array into skin.

2. The microstructure apparatus of claim 1, wherein the at least one therapeutic agent is a small molecule drug at least partially soluble with the at least one polymer in a solvent or co-solvent.

3. The microstructure apparatus of claim 1, where the at least one therapeutic agent is dispersed in the distal layer.

4. The microstructure apparatus of claim 1, where at least about 10% of the distal layer detaches readily upon the insertion of the array into the skin.

5. The microstructure apparatus of claim 1, where at least about 50% of the distal layer detaches readily upon the insertion of the array into the skin.

6. The microstructure apparatus of claim 1, where at least about 70% of the distal layer detaches readily upon the insertion of the array into the skin.

7. The microstructure apparatus of claim 1, where at least about 90% of the distal layer detaches readily upon the insertion of the array into the skin.

8. The microstructure apparatus of claim 1, where about 100% of the distal layer detaches readily upon the insertion of the array into the skin.

9. The microstructure apparatus of claim 1, where at least a portion of the plurality of microstructures have a first cross-dimensional diameter that is larger than a second cross-dimensional diameter.

10. The microstructure apparatus of claim 9, where at least a portion of the plurality of microstructures have a cross-dimensional shape selected from the group consisting of a diamond, a rectangle, and an oval.

11. The microstructure apparatus of claim 9, where at least a portion of the plurality of microstructures have a cross-dimensional shape selected from rectangular, square, oval, elliptical, circular, and polygonal.

12. The microstructure apparatus of claim 1, wherein at least a portion of the at least one proximal layer, at least a portion of the distal layer, or at least portions of both the at least one proximal layer and the distal layer have a funnel shape.

13. The microstructure apparatus of claim 1, wherein the plurality of microstructures are affixed to the first surface of the backing.

14. The microstructure apparatus of claim 1, wherein at least a portion of the backing forms the at least one proximal layer.

15. The microstructure apparatus of claim 1, further comprising a substrate having a first surface and a second surface opposed thereto, where the second surface of the backing is affixed to the first surface of the substrate.

16. The microstructure apparatus of claim 1, where the at least one polymer of the distal layer comprises at least one hydrophobic polymer and about 0-50% of a hydrophilic polymer.

17. The microstructure apparatus of claim 1, where the at least one polymer of the distal layer comprises at least one hydrophobic polymer and about 0-20% of a hydrophilic polymer.

18. The microstructure apparatus of claim 1, wherein about 1-99% of the distal layer is comprised of the at least one therapeutic agent.

19. The microstructure apparatus of claim 18, wherein 1-90% of the distal layer is comprised of the at least one therapeutic agent.

20. The microstructure apparatus of claim 18, wherein the at least one therapeutic agent is a small molecule drug at least partially soluble with the at least one polymer in a solvent or co-solvent.

21. The microstructure apparatus of claim 20, wherein about 1-50% of the distal layer is comprised of the small molecule drug.

22. The microstructure apparatus of claim 20, wherein about 1-40% of the distal layer is comprised of the small molecule drug.

23. The microstructure apparatus of claim 20, wherein about 10-30% of the distal layer is comprised of the small molecule drug.

24. The microstructure apparatus of claim 18, where the at least one therapeutic agent is dispersed in the distal layer.

25. The microstructure apparatus of claim 24, wherein about 1-90% of the distal layer is comprised of the at least one dispersed therapeutic agent.

26. The microstructure apparatus of claim 24, wherein about 1-50% of the distal layer is comprised of the at least one dispersed therapeutic agent.

27. The microstructure apparatus of claim 24, wherein about 10-40% of the distal layer is comprised of the at least one dispersed therapeutic agent.

28. The microstructure apparatus of claim 24, wherein about 20-30% of the distal layer is comprised of the at least one dispersed therapeutic agent.

29. The microstructure apparatus of claim 1, wherein the at least one polymer has a glass transition temperature (Tg) above about body temperature.

30. The microstructure apparatus of claim 1, wherein the at least one polymer has a molecular weight of about 1-100K Da.

31. The microstructure apparatus of claim 1, wherein at least about 10-100% of the distal layer is configured to detach readily upon the insertion of the array into the skin.

32. The microstructure apparatus of claim 1, wherein the hydrophobic polymer is insoluble in aqueous solvents.

33. A method of making the microstructure apparatus of claim 1, comprising:

dissolving or suspending a therapeutic agent in a solvent to form a therapeutic agent solution or suspension;

dissolving at least one polymer in a solvent to form a polymer solution;

mixing the therapeutic agent solution or suspension and the polymer solution or suspension to form a polymer matrix solution or suspension;

dispensing the polymer matrix solution or suspension on a mold having an array of microstructure cavities; followed by pressurization;

removing excess solution or suspension polymer matrix on the mold surface; and drying the matrix; and dispensing a basement or backing layer on the mold surface; and drying the basement or backing layer.

34. The method of claim 33, further comprising:

affixing the basement or backing layer to a substrate.

35. The method of claim 34 further comprising:

using a nonwoven or porous film double coated with adhesive to affix the basement or backing layer to a substrate.

* * * * *

UNITED STATES PATENT AND TRADEMARK OFFICE
CERTIFICATE OF CORRECTION

| | | |
|---|---|---|
| PATENT NO. | : 11,052,231 B2 | Page 1 of 1 |
| APPLICATION NO. | : 14/137899 | |
| DATED | : July 6, 2021 | |
| INVENTOR(S) | : Ding et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 386 days.

Signed and Sealed this
Twentieth Day of December, 2022

*Katherine Kelly Vidal*

Katherine Kelly Vidal
*Director of the United States Patent and Trademark Office*